US008333955B2

(12) United States Patent
Tabakman et al.

(10) Patent No.: US 8,333,955 B2
(45) Date of Patent: Dec. 18, 2012

(54) HIGH SHINE, STICK-SHAPED COSMETIC PRODUCTS

(75) Inventors: Tatyana R. Tabakman, Brooklyn, NY (US); George J. Stepniewski, Melville, NY (US); John R. Castro, Huntington Station, NY (US); Cecilia D. Benedicto, Plainview, NY (US); Kathleen McKerlie, Bethpage, NY (US); Anne T. Carullo, New York, NY (US)

(73) Assignee: ELC Management LLC, New York, NY (US)

( * ) Notice: Subject to any disclaimer, the term of this patent is extended or adjusted under 35 U.S.C. 154(b) by 374 days.

(21) Appl. No.: 11/687,876

(22) Filed: Mar. 19, 2007

(65) Prior Publication Data

US 2008/0233064 A1    Sep. 25, 2008

(51) Int. Cl.
*A61K 8/00* (2006.01)
*A61K 31/74* (2006.01)
(52) U.S. Cl. ........................................ 424/64; 424/78.03
(58) Field of Classification Search .................. None
See application file for complete search history.

(56) References Cited

U.S. PATENT DOCUMENTS

| | | | |
|---|---|---|---|
| 4,699,780 A | 10/1987 | Jennings et al. | |
| 5,225,186 A | 7/1993 | Castrogiovanni et al. | |
| 5,480,632 A * | 1/1996 | Orr et al. ........................ | 424/63 |
| 5,505,937 A | 4/1996 | Castrogiovanni et al. | |
| 6,086,859 A | 7/2000 | Calello et al. | |
| 6,103,250 A | 8/2000 | Brieva et al. | |
| 6,143,283 A | 11/2000 | Calello et al. | |
| 2004/0202627 A1 * | 10/2004 | Kuroda et al. ................. | 424/63 |
| 2006/0008489 A1 | 1/2006 | Egawa et al. | |
| 2006/0019848 A1 | 1/2006 | Luo et al. | |
| 2006/0051307 A1 | 3/2006 | Gotou et al. | |
| 2006/0165640 A1 * | 7/2006 | Lebre et al. ................. | 424/70.22 |
| 2007/0110702 A1 * | 5/2007 | Ehara .......................... | 424/70.31 |

FOREIGN PATENT DOCUMENTS

| | | | |
|---|---|---|---|
| EP | 1 905 411 | | 4/2008 |
| JP | 2004-107355 | | 4/2004 |
| WO | WO 2006/003992 | * | 1/2006 |
| WO | WO2006/003992 | | 12/2006 |
| WO | WO 2006/134896 | | 12/2006 |
| WO | WO2008/115776 | | 9/2008 |

OTHER PUBLICATIONS

Danoux et al., Cosmetics & Toiletries, 2005, 120(12), pp. 63-72.*
PCT International Search Report; International Application No. PCT/US08/056963; Completion Date: Jul. 28, 2008; Date of Mailing: Jul. 28, 2008.
PCT Written Opinion of the International Searching Authority, or the Declaration; International Application No. PCT/US08/056963; Completion Date: Jul. 28, 2008; Mailing Date: Jul. 28, 2008.

* cited by examiner

*Primary Examiner* — Brian Gulledge
(74) *Attorney, Agent, or Firm* — Cynthia Miller

(57) ABSTRACT

The present invention provides a cosmetic composition having a gloss of at least about 85 gloss units (gu), as well as sufficient shape retention properties for forming a stick-shaped cosmetic product. Specifically, the cosmetic composition contains: (a) a high viscosity oil component; (b) a medium viscosity oil component; (c) a low viscosity oil component; and (d) an oily gelling agent comprising an ester of glycerol or polyglycerin with an aliphatic or hydroxyl aliphatic acid and a dibasic acid. A stick-shaped cosmetic product formed by the cosmetic composition of the present invention exhibits a high-shine that is not available in conventional stick-shaped cosmetic products and yet retains the high make-up coverage typically provided by conventional stick-shaped cosmetic products.

17 Claims, No Drawings

HIGH SHINE, STICK-SHAPED COSMETIC PRODUCTS

FIELD OF THE INVENTION

The present invention relates to a cosmetic composition suitable for forming stick-shaped cosmetic products, such as lipsticks, foundation sticks, blush sticks, eye shadow sticks, and the like. The stick-shaped cosmetic products so formed are characterized by an exceptional shine that is not available in conventional stick-shaped cosmetic products.

BACKGROUND OF THE INVENTION

When women are asked what cosmetic item they simply could not be without, a typically high percentage reply that lip color is an essential item of their beauty wardrobe. Lip products come in a variety of forms, which vary depending upon the look desired by the user. The products may be highly pigmented, pearlescent, matte, or glossy/shiny. The high gloss/shine type of lip color is currently particularly popular. The look conferred by such a product is highly glamorous and sensual.

However, the conventional lip color compositions with high gloss/shine are typically in liquid form (e.g., liquid lip gloss) or semi-solid form (e.g., lip cream or lip paste), which are too soft or "runny" for use in forming free-standing lipsticks. Further, such conventional lip gloss, lip cream, and lip paste do not provide sufficiently high make-up coverage and therefore are usually applied as a top coat over a conventional matte lipstick to provide the desired gloss/shine. In comparison, the conventional solid lip color compositions that are suitable for forming free-standing lipsticks with sufficient make-up coverage typically produce relatively opaque, dull coatings that are characterized by significantly lower gloss/shine.

It is therefore desirable to provide an improved cosmetic composition that has a high gloss/shine similar to that of the conventional liquid lip gloss or semi-solid lip cream/paste, which also has sufficient shape retention characteristics for forming free-standing, stick-shaped cosmetic products and provides high make-up coverage close to that provided by conventional matte lipsticks. It is also desirable to provide an improved cosmetic composition that has excellent spreadability, provides a unique cushioned, luxurious feel, and is therefore comfortable to wear.

SUMMARY OF THE INVENTION

In one aspect, the present invention relates to a cosmetic composition that contains at least:
(a) a high viscosity oil component having a first viscosity;
(b) a medium viscosity oil component having a second viscosity that is lower than the first viscosity;
(c) a low viscosity oil component having a third viscosity that is lower than the second viscosity; and
(d) an oily gelling agent comprising an ester of glycerol or polyglycerin with an aliphatic or hydroxyl aliphatic acid and a dibasic acid,
wherein the cosmetic composition is characterized by a gloss of not less than about 85 gloss unit (gu) and has sufficient shape retention properties for forming a stick-shaped cosmetic product.

Preferably, the first viscosity ranges from about 100 centipoises to about 300 centipoises at about 25° C.; the second viscosity ranges from about 10 centipoises to about 100 centipoises at about 25° C.; and the third viscosity ranges from about 0.1 centipoise to about 100 centipoises at about 25° C. More preferably, the first viscosity ranges from about 150 centipoises to about 250 centipoises at about 25° C.; the second viscosity ranges from about 50 centipoises to about 80 centipoises at about 25° C.; and the third viscosity ranges from about 5 centipoise to about 30 centipoises at about 25° C.

The term "gloss unit" as used herein is a unit for quantifying the gloss or shine of a cosmetic composition or product, which is specifically determined by the testing method described hereafter in Example 2. The term "shape retention properties" as used herein refers to the capability of a cosmetic composition or product in maintaining a specific shape that it is originally molded or otherwise formulated into, free of any structural support from external devices or means. Such shape retention properties may be defined by various different parameters. Preferably, the shape retention properties of the cosmetic composition of the present invention is defined by a drop point of not less than 50° C., more preferably not less than 60° C., and most preferably not less than 70° C.

In another aspect, the present invention relates to a stick-shaped cosmetic product formed by the cosmetic composition described hereinabove. Specifically, such a stick-shaped cosmetic product is characterized by a drop point of not less than about 70° C. Such a stick-shaped cosmetic product may further be characterized by: (a) a breakage point of not less than about 10 pounds, and/or (b) a crush point of not less than about 2 kilograms.

In yet another aspect, the present invention relates to a cosmetic composition comprising:
(a) from about 20 wt % to about 80 wt % of a high viscosity oil component having a first viscosity ranging from about 100 centipoises to about 300 centipoises at about 25° C.;
(b) from about 0.1 wt % to about 5 wt % of a medium viscosity oil component having a second viscosity that is lower than the first viscosity, said second viscosity ranging from about 10 centipoises to about 100 centipoises at about 25° C.;
(c) from about 0.1 wt % to about 5 wt % of a low viscosity oil component having a third viscosity that is lower than the second viscosity, said third viscosity ranging from about 0.1 centipoises to about 100 centipoises at about 25° C.; and
(d) from about 0.1 wt % to about 5 wt % of an oily gelling agent comprising an ester of glycerol or polyglycerin with an aliphatic or hydroxyl aliphatic acid and a dibasic acid.

In a still further aspect, the present invention relates to a method of forming a stick-shaped cosmetic product, comprising the steps of:
(a) forming a cosmetic composition comprising a high viscosity oil component having a first viscosity, a medium viscosity oil component having a second viscosity that is lower than the first viscosity, a low viscosity oil component having a third viscosity that is lower than the second viscosity, and an oily gelling agent comprising an ester of glycerol or polyglycerin with an aliphatic or hydroxyl aliphatic acid and a dibasic acid, wherein said cosmetic composition is characterized by a gloss of not less than about 85 gloss unit (gu) and has sufficient shape retention properties for forming the stick-shaped cosmetic product;
(b) pouring said cosmetic composition into a mold having one or more stick-shaped cavities; and (c) allowing the cosmetic composition to solidify in the mold, thereby forming one or more stick-shaped cosmetic products.

Other aspects and objectives oaf the present invention will become more apparent from the ensuing description, examples, and claims.

DETAILED DESCRIPTION OF THE INVENTION AND PREFERRED EMBODIMENTS THEREOF

The cosmetic compositions of the present invention comprise four basic elements: a high viscosity oil component, a medium viscosity oil component, and a low viscosity oil component blended with an oily gelling agent containing an ester of glycerol or polyglycerin with an aliphatic or hydroxyl aliphatic acid and a dibasic acid. The combination of these four elements results in a highly viscous composition with sufficient shape retention characteristics suitable for forming a stick-shaped cosmetic product with high shine/gloss.

The oily gelling agent as used in the present invention is formed by esterifying: (1) a straight or branched aliphatic acid or a hydroxy aliphatic acid having 8-30 carbon atoms, which can be either saturated or unsaturated, (2) a straight or branched dibasic acid having 12-36 carbon atoms, and (c) glycerol or polyglycerin, according to esterification methods well known in the art. Exemplary aliphatic or hydroxyl aliphatic acids suitable for forming the oily gelling agent of the present invention include, but are not limited to: oleic acid, myristic acid, palmitic acid, lauric acid, stearic acid, behenic acid, isostearic acid, 12-hydroxystearic acid, octanoic acid, and the like. Exemplary dibasic acids suitable for forming the oily gelling agent of the present invention include, but are not limited to: eicosanoic diacid, 1,7-ethyloctadecane diacid, dodecane diacid, and the like. Glycerol or any polyglycerin with a polymerization degree of 2 or more can be used for forming the oily gelling agent of the present invention. When polyglycerin is used, it is preferred that the polymerization degree of such polyglycerin ranges from 2 to 10. In a particularly preferred embodiment of the present invention, the oily gelling agent comprises the glycerol ester of behenic acid and eicosanoic diacid, which is commercially available under the trade name "Nomcort HK-G" from Nisshin Oillio Co., Ltd. (Tokyo, Japan).

The oily gelling agent as described hereinabove is typically present in the cosmetic composition of the present invention at an amount ranging from about 0.1 wt % to about 5 wt %, preferably from about 0.5 wt % to about 2 wt %. The oily gelling agent may also be provided at amounts beyond the above-specified ranges, depending on the desired product requirements.

The high viscosity oil component as used in the present invention may be any naturally-occurring or synthetic oil suitable for use in cosmetic compositions with a viscosity of not less than 100 centipoises. Preferably, the high viscosity oil has a first viscosity ranging from about 100 centipoises to about 300 centipoises at about 25° C., more preferably from about 150 centipoises to about 250 centipoises. Examples of such high viscosity oils include, but are not limited to: tridecyl trimellitate, diisostearyl malate, triisostearyl citrate, polyglyceryl-2-triisostearate, and combinations thereof. In a particularly preferred embodiment of the present invention, the high viscosity oil component comprises tridecyl trimellitate, which is commercially available, among others, under the trade name "Liponate TD™" from Lipo Chemicals Inc. at Paterson, N.Y.

The high viscosity oil component as described hereinabove is typically present in the cosmetic composition of the present invention at an amount ranging from about 20 wt % to about 80 wt %, preferably from about 40 wt % to about 60 wt %. The high viscosity oil component may also be provided at amounts beyond the above-specified ranges, depending on the desired product requirements. However, it may be important to maintain the concentration of the high viscosity oil component at not less than about 10 wt %, because when the concentration of the high viscosity oil is below 10 wt %, additional thickeners or binders may be needed to provide sufficient viscosity and shape retention properties, while such additional thickeners or binders can adversely affect the gloss/shine of the resulting cosmetic composition. Further, certain thickeners or binders are not compatible with the oily gelling agent, and addition of such non-compatible thickeners or binders may destroy the consistency and structural integrity of the cosmetic composition, resulting in a composition that cannot be molded into stick-shaped products.

The medium viscosity oil component as used in the present invention may be any naturally-occurring or synthetic oil suitable for use in cosmetic compositions with a viscosity ranging from about 10 centipoises to about 100 centipoises at about 25° C. Examples of such medium viscosity oils include, but are not limited to: caprylic/capric triglyceride, penthaerythrityl tetraisostearate, octyldodecyl lactate, PPG-3 benzyl myristate ether, and combinations thereof. In a particularly preferred embodiment of the present invention, the medium viscosity oil component comprises caprylic/capric triglyceride, which is commercially available, among others, under the trade name "Crodasperse" from Croda Inc. at Edison, N.J.

The medium viscosity oil component as described hereinabove is typically present in the cosmetic composition of the present invention at an amount ranging from about 0.1 wt % to about 5 wt %, preferably from about 0.5 wt % to about 2 wt %.

The low viscosity oil component as used in the present invention may be any naturally-occurring or synthetic oil suitable for use in cosmetic compositions with a viscosity ranging from about 0.1 centipoises to about 100 centipoises at about 25° C., provided that the viscosity of the low viscosity oil component is lower than the viscosity of the medium viscosity oil component in any given composition of the present invention. In other words, a specific oil component may be used as the low viscosity oil component in one composition, but as the medium viscosity oil component in another composition, as long as said another oil composition contains an additional oil component with a lower viscosity to function as the low viscosity oil therein. Examples of suitable low viscosity oils include, but are not limited to: octyldodecyl neopentanoate, tridecyl octanoate, isopropyl isostearate, isodecyl isononanoate, and combinations thereof. In a particularly preferred embodiment of the present invention, the low viscosity oil component comprises octyldodecyl neopentanoate, which is commercially available, among others, under the trade name "ELEFAC I-205" from Bernel Chemical Company at Tenafly, N.J.

The low viscosity oil component as described hereinabove is typically present in the cosmetic composition of the present invention at an amount ranging from about 0.1 wt % to about 5 wt %, preferably from about 0.5 wt % to about 2 wt %. Preferably, but not necessarily, the weight ratio between the medium viscosity oil and the low viscosity oil in the present invention ranges from about 1:5 to about 10:1, more preferably from about 1:1 to about 3:1.

Although not wishing to be bound by any particular theory, it is believed by the inventors that the combined use of the three oil components with different viscosities, as described hereinabove, are important for providing a cosmetic composition with sufficient shape retention characteristics for forming a stick-shaped cosmetic product as well as sufficient consistency. The high viscosity oil component is believed to improve the overall viscosity of the cosmetic composition for better product shape retention, while the medium and low viscosity oil components are believed to provide a viscosity gradient in conjunction with the high viscosity oil component, which leads to better compatibility between the different oil components and the oily gelling agent and ultimately improves the overall consistency and structural integrity of the resulting cosmetic composition.

The shape retention properties of the cosmetic composition so formed may be defined by various different parameters. For example, the drop point of the cosmetic composition may be used for defining the shape retention properties thereof, and preferably, the cosmetic composition of the present invention is characterized by a drop point of not less than 50° C., more preferably not less than 60° C., and most preferably not less than 70° C.

Waxes that are typically used for increasing the shape retention properties of cosmetic compositions may optionally be used in the composition of the present invention. However, since a high wax concentration may destroy the gloss or shine of the composition, it is preferred to keep the total amount of waxes in the composition of the present invention below 10%, more preferably below 8%. Suitable waxes that can be used in the present invention include, but are not limited to: candelilla, carnauba waxes, beeswax, spermaceti, carnauba, baysberry, montan, ozokerite, ceresin, paraffin, synthetic waxes such as Fisher-Tropsch waxes, silicone waxes (e.g., DC 2503 from Dow Corning), microcrystalline waxes, and the like.

The cosmetic composition of the present invention may further comprise one or more polymeric gels for providing cushioning and moisturizing effects and improving spreadability of the resulting cosmetic composition. Any polymeric gel with a sufficient water retention rate (e.g., not less than about 50% by its original weight) can be used in the present invention. Suitable polymeric gels include, but are not limited to: bis-diglyceryl polyacyladipate-2, dipentaerythrityl tetrabehenate/polyhydroxystearate, dextrin palmitate, dibutyl lauroyl glutamate, ethyl cellulose, and the like. More specifically, dipentaerythrityl tetrabehenate/polyhydroxystearate, which is commercially available in form of a blend with behenic acid and hydroxystearic acid under the trade name "Pelemol DP-144B" from Phoenix Chemical, Inc. at Somerville, N.J., provides longer wear and is therefore particularly preferred in the cosmetic composition of the present invention. The total amount of polymeric gels in such composition may range from about 2 wt % to about 40%, depending on the specific product requirements. In a particularly preferred embodiment of the present invention, the cosmetic composition contains from about 5 wt % to about 10 wt % of bis-diglyceryl polyacyladipate-2 and from about 5 wt % to about 10 wt % of dipentaerythrityl tetrabehenate/polyhydroxystearate.

When used for forming stick-shaped lip products, the cosmetic composition of the present invention may further comprise a pasty component having a melting temperature or a drop point ranging from about 32° C. to about 42° C. Such pasty component with its melting temperature or drop point close to the average human body temperature allows the resulting composition to soften upon application onto the lips and thereby provides a smooth and comfortable butter-like feel. Suitable pasty components that can be used in the cosmetic composition of the present invention include, but are not limited to: caprylic/capric/myristic/stearic triglyceride, cetyl lactate, lanolin, shea butter, and the like. In a particularly preferred embodiment of the present invention, the pasty component comprises caprylic/capric/myristic/stearic triglyceride, which is commercially available, among others, under the trade name "Softisan 378" from SASOL North America Inc. at Houston, Tex. The pasty component as described hereinabove may be present in the cosmetic composition of the present invention at an amount ranging from about 2 wt % to about 20 wt %, more preferably from about 5 wt % to about 10 wt %.

In order to further improve the appearance and comfort of the cosmetic composition of the present invention, one or more film formers are preferably employed therein. Preferably, such composition includes both a liquid film former and a solid film former. Combination of both liquid and solid film formers creates a flexible and breathable film, prevents feathering and color disappearance of the resulting cosmetic product, and thereby optimizes the product performance. Suitable liquid film formers for use in the present invention may include, but are not limited to: PVP/hexadecene copolymer, polyglyceryl-2 diisostearate/isophorone diisocyanate (IPDI) copolymer, synthetic wax (e.g., Performa V-825 available from Phase Technologies at Piscataway, N.J.), methyl hydrogenated rosinate, and the like. Such liquid film former(s) may be present at an amount ranging from about 0.01 wt % to about 2 wt %. Suitable solid film formers may include, but are not limited to: PVP/eicosene copolymer, tricontanyl PVP, $C_{20}$-$C_{40}$ alcohols, glyceryl rosinate, and the like. Such solid film former(s) it may be present at an amount ranging from about 0.5 wt % to about 5 wt %. In a particularly preferred embodiment of the present invention, the cosmetic composition contains from about 0.1 wt % to about 0.5 wt % of PVP/hexadecene and from about 1 wt % to about 2 wt % of PVP/eicosene copolymer.

The cosmetic composition of the present invention may further comprises one or more sugar gellants formed by reacting a saturated or unsaturated $C_{12}$-$C_{22}$ fatty acid with a sugar or alkylsugar in which the alkyl group contains from about 1 to 8 carbon atoms. The sugar is preferably a monosaccharide or oligosaccharide. Examples of suitable sugar gellants for use in the present invention include, but are not limited to: alkyl glucose sesquistearates (such as methyl glucose sesquistearate), alkyl glucose palmitates (such as methyl glucose palmitate and ethyl glucose palmitate), sucrose monolaurate, glucose palmitate, as well as PEG or PPG derivatives of such compounds. The amount of sugar gellant(s) used in the cosmetic composition of the present invention may range from about 0.1 wt % to about 10 wt %, preferably from about 0.5 wt % to about 5 wt %.

If the composition of the present invention is designed to be used in a color cosmetic, such as lip sticks, blush sticks, eye shadow sticks, and the like, and it will also contain one or more organic and/or inorganic pigments. Examples of suitable inorganic pigments include, but are not limited to: iron oxides (yellow, red, brown or black), titanium dioxide (white), zinc oxide, chrome oxide (green), chrome hydrate (green), ultramarines, manganese violet, ferric ferrocyanide, carmine 40, ferric ammonium ferrocyanide, or combinations thereof. Interference pigments, which are thin platelike layered particles having a high refractive index, and which, at a certain thickness, produce interference colors, resulting from the interference of typically two, but occasionally more light reflections from different layers of the plate, can also be added to provide a pearlescence to the product. Suitable organic pigments for use in the composition of the present invention include, but are not limited to: natural colorants, synthetic monomeric and polymeric colorants, such as phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C Lakes and blends thereof. Stains, such as bromo dyes and fluorescein dyes can also be employed. The cosmetic composition may also contain one or more types of cosmetically acceptable glitter, i.e., particles of transparent or colored, solid organic materials, such as poly(ethylene terephthalate), polymethacrylate, and poly (vinylbutyral), particles of metal, or particles of metal coated film or paper.

The total amount of pigments in the cosmetic composition of the present invention may range from about 0.1 wt % to about 30 wt %. For color cosmetic products, it is preferable to employ a larger amount of pigments, e.g., from about 5 wt % to about 30 wt %, more preferably from about 10 wt % to about 20 wt %, in the composition.

The cosmetic compositions of the present invention can also contain inorganic powders, such as soft focus powders, or plate-like non-spherical powders such as bismuth oxychloride, boron nitride, barium sulfate, mica, sericite, muscovite, synthetic mica, titanium oxide coated mica, titanium oxide-coated bismuth oxychloride, titanium oxide coated talc, platelet iron oxides, metal powders such as aluminum, lauroyl lysine and platelet talc. Amounts of such inorganic powders are not critical, but if used, typically will be used in an amount of about 0.5 to about 5%.

The cosmetic composition of the present invention may further contain one or more skin care active ingredients or skin care actives. The term "skin care active ingredients" or "skin care actives" as used herein refers to agents that provide benefits to the skin rather than merely improving the physical characteristics of the cosmetic composition. For example, the cosmetic composition may comprise anti-aging agents, free radical scavenging agents, lipid peroxidation preventing agents, lipogenase inactivating agents, agents that inhibit undesired enzymatic activities, and agents that stimulate collagen synthesis. The cosmetic composition may also include sunscreen agents, antioxidants, exfoliants, analgesics, anesthetics, antibacterials, antiyeast agents, antifungal agents, antiviral agents, antidermatitis agents, antipruritic agents, antiemetics, anti-inflammatory agents, antihyperkeratolytic agents, antiperspirants, antipsoriatic agents, antiseborrheic agents, antiwrinkle agents, antihistamine agents, vitamins, corticosteroids, self-tanning agents, hormones, retinoids such as retinoic acid and retinol, topical cardiovascular agents, clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, topical steroids such as hydrocortisone, hydrocortisone 21-acetate, hydrocortisone 17-valerate, and hydrocortisone 17-butyrate, betamethasone valerate, betamethasone diproprionate, benzoyl peroxide, crotamiton, propranolol, promethazine, vitamin A palmitate, vitamin E acetate and mixtures thereof. The above-described skin care active ingredients are only optional components of the cosmetic composition of the present invention and may be omitted from such composition without materially affecting the intended functions of the cosmetic composition.

Additional substances which may be formulated into the cosmetic composition of the present application include, but are not limited to: moisturizing agents, astringent agents, chelating agents, surfactants, emollients, preservatives, stabilizers, thickeners, humectants, pigments, and the like.

For example, emollients which may be used in the cosmetic composition of the present invention include, but are not limited to: stearyl alcohol, cetyl alcohol, oleyl alcohol, isocetyl alcohol, fatty alcohols, propane-1,2-diol, butane-1, 3-diol, octadecan-2-ol, glyceryl monostearate, isopropyl isostearate, stearic acid, isostearic acid, isocetyl stearate, isopropyl stearate, butyl stearate, isopropyl laurate, hexyl laurate, decyl oleate, isobutyl palmitate, cetyl palmitate, isopropyl palmitate, palmitic acid, dimethylpolysiloxane, glyceryl monoricinoleate, di-n-butyl sebacate, isopropyl myristate, butyl myristate, myristyl myristate, isopropyl linoleate, lauryl lactate, myristyl lactate, polyethylene glycol, triethylene glycol, lanoline, acetylated lanolin, sesame oil, coconut oil, arrachis oil, castor oil, mink oil, mineral oil, and petroleum.

A variety of water soluble preservatives can be added to the cosmetic compositions of the present invention to provide a prolonged shelf life. Suitable preservatives include, but are not limited to: potassium sorbate, imidazolidinyl urea, p-hydroxy benzoate, esters of p-hydroxybenzoic acid, CTFA designation parabens, ethylhexylglycerin, caprylyl glycol/phenoxyethanol/hexylene glycol, and the like. Other preservatives suitable for use in the cosmetic compositions of the present invention are disclosed in the International Cosmetic Ingredient Dictionary and Handbook, twelfth edition, 2004, the entire disclosure of which is herein incorporated by reference.

Humectants which may be used include, but are not limited to: polyhydric alcohols including glycerol, polyalkylene glycols, and alkylene polyols and mixtures thereof, hyaluronic acid, urea, glycerin, sorbitol, sodium 2-pyrrolidone-5-carboxylate, soluble collagen, dibutylphthalate and gelatin.

The cosmetic composition of the present invention may optionally comprise a fragrance in an amount sufficient to make the composition more appealing to the consumer. Preferably, the fragrance is in the amount of from about 0.01% to about 10% by total weight of the composition.

Although the most preferred embodiment of the invention is an anhydrous, oil-based composition, it is possible to utilize the compositions of the invention as the oil-phase of a water and oil emulsion. When used as the oil phase of an emulsion, the composition's water phase can also contain water soluble actives. Furthermore, although a particularly preferred use of the cosmetic compositions of the present invention is in forming lipsticks, it may also be used for forming other types of stick-shaped cosmetic products, such as, for example, foundation sticks, blush sticks, eye shadow sticks, eyeliners, body make-up sticks, and the like.

Such stick-shaped cosmetic products can be readily manufactured by processes conventionally used to make stick-shaped cosmetics. In particular, the stick-shaped cosmetic products of the present invention may be formed by the following steps:

(a) forming the above-described cosmetic composition via one or more mixing steps;

(b) pouring the cosmetic composition into a mold having one or more stick-shaped cavities; and (c) allowing the cosmetic composition to solidify in the mold, thereby forming one or more stick-shaped cosmetic products.

The stick-shaped cosmetic products formed from the above-described cosmetic composition is typically characterized by a drop point of not less than about 50° C., more typically not less than about 60° C., and most typically not less than about 70° C. Further, the stick-shaped cosmetic products may be characterized by: (1) a relatively high breakage point (e.g., at least about 10 pounds); and/or (2) a relatively high crush point (e.g., at least about 2 kilograms). Most preferably, the stick-shaped cosmetic products of the present invention have a drop point of more than 75° C., a breakage point of more than 12 pounds, and a crush point of more than 2.2 kilograms.

The following examples further illustrate various specific embodiments of the present invention, without limiting the broad scope thereof.

EXAMPLE 1

High-Shine Lipstick Compositions

FORMULA I

| Phases | Components | Wt % |
|---|---|---|
| Phase A | Tridecyl trimellitate | 11.8575 |
| | Caprylic/capric/myristic/stearic triglyceride | 10.0000 |
| | Dipentaerythrityl tetrabehenate/polyhydroxystearate//behenic acid//hydroxystearic acid | 7.0000 |
| | Bis-diglyceryl polyacyladipate-2 | 5.0000 |
| | Polyethylene (linear)/microcrystalline wax | 3.0000 |
| | Polyethylene (cross-linked) | 3.0000 |
| | Ozokerite | 3.0000 |
| | Caprylic/capric triglyceride//DI-PPG-3 myristyl ether adipate//sorbitan isostearate | 2.0000 |
| | PVP/eicosene copolymer | 1.4000 |
| | Tocopheryl acetate | 1.1425 |
| | Methyl glucose sesquistearate | 1.0000 |
| | Octyldodecyl neopentanoate | 1.0000 |
| | Glyceryl behenate/eicosadioate | 0.5000 |
| | PVP/hexadecene copolymer | 0.1000 |
| Phase B | Tridecyl trimellitate | 20.4390 |
| Phase C | Mica | 3.0000 |
| | Polymethyl methacrylate | 1.0000 |
| | Mica/titanium dioxide | 1.0000 |
| Phase D | Tridecyl trimellitate | 15.6735 |
| | Titanium dioxide | 4.2598 |
| | Iron oxides (Red) | 1.9185 |
| | Iron oxides (Russet) | 1.2794 |
| | D&C Red No. 7 calcium lake | 0.4277 |
| | FD&C Yellow No. 5 aluminum lake | 0.4253 |
| | FD&C Blue No. 1 aluminum lake | 0.1944 |
| | Tocopheryl acetate | 0.1215 |
| Phase E | Cholesterol/potassium sulfate | 0.0010 |
| | Wheat bran extract/olive extract | 0.0500 |
| | Squalane/Barley extract/wheat germ extract | 0.0100 |
| | Linoleic acid | 0.1000 |
| Phase F | Vanillin | 0.0500 |
| | Fragrance | 0.0500 |

FORMULA II

| Phases | Components | Wt % |
|---|---|---|
| Phase A | Tridecyl trimellitate | 29.1588 |
| | PVP/hexadecene copolymer | 0.1000 |
| | Octyldodecyl neopentanoate | 0.5000 |
| | Caprylic/capric triglyceride//DI-PPG-3 myristyl ether adipate//sorbitan isostearate | 1.0000 |
| | Tocopheryl acetate | 1.1287 |
| | Caprylic/capric/myristic/stearic triglyceride | 6.5000 |
| | Dipentaerythrityl tetrabehenate/polyhydroxystearate//behenic acid//hydroxystearic acid | 8.0000 |
| | Bis-diglyceryl polyacyladipate-2 | 9.0000 |
| Phase B | Methyl glucose sesquistearate | 1.0000 |
| | Glyceryl behenate/eicosadioate | 1.0000 |
| | Polyethylene (linear)/microcrystalline wax | 3.0000 |
| | Polyethylene (cross-linked) | 3.0000 |
| | Ozokerite | 3.0000 |
| | PVP/eicosene copolymer | 1.4000 |
| Phase C | Tridecyl trimellitate | 7.8328 |
| | Tocopheryl acetate | 0.0619 |
| | Titanium dioxide | 1.7908 |
| | D&C Red No. 7 calcium lake | 0.4125 |
| | Iron oxides (yellow) | 0.2684 |
| | Iron oxides (red) | 1.8172 |
| | Iron oxides (black) | 0.1914 |
| Phase D | Mica | 1.5000 |
| | Polymethyl methacrylate | 1.0000 |
| | Calcium aluminum borosilicate/silica/titanium dioxide/tin oxide | 1.7160 |
| Phase E | Tridecyl trimellitate | 7.1400 |
| | Barium sulfate | 4.8000 |
| | Tocopheryl acetate | 0.0600 |
| Phase F | Cholesterol/potassium sulfate | 0.0010 |
| | Wheat bran extract/olive extract | 0.0500 |
| | Squalane/Barley extract/wheat germ extract | 0.0100 |
| | Linoleic acid | 0.1000 |
| Phase G | Calcium sodium borosilicate/titanium dioxide | 0.0001 |
| | Polyethylene terephthalate/acrylates copolymer | 0.0001 |
| | Copper powder/silica | 0.0001 |
| | Silica/titanium dioxide/tin oxide | 0.0001 |
| | Synthetic fluorphlogopite/iron oxides | 0.0001 |
| Phase H | Tridecyl trimellitate | 3.0000 |
| Phase I | Vanillin | 0.0500 |
| | Fragrance | 0.0500 |

Pigments of Phase C and Phase E in Formula II were pre-dispersed in the blend of main liquid and Vitamin E (antioxidant) at room temperature prior to grinding through roller mill or ball mill. Quality of the finest grind was checked on Hegman Gauge scale (scale from 0-10). The best results were in between 7 to 8. Ingredients of the Phase A were placed into appropriate size beaker equipped with propeller type agitator and heated up to 90° C., with medium mixing speed to avoid product aeration and spilling for at least 20 minutes. Ingredients of Phase B were slowly added and mixed for 10 minutes until mass was clear. The temperature was then lowered to 85° C., and fine grind of Phase C was added into the mixture and mixed well until all uniform without any color streaks observed. The temperature was kept the same at 85° C., and Phases D and G were added into the mixture and mixed well until all wetted without any dry powder floating. Phases E and H were used for color adjustments (in case of shade adjustments, take part of Phase E or H respectfully to come out with 100% formula). Phases F and I were added right before dropping the batch and after shade matching process was finished. The final batch was molded into lipsticks immediately or was stored in close containers and re-melted before filling into the molds. The molding temperature was maintained at about 80-85° C.

EXAMPLE 2

Gloss Measurement

A lipstick formed according to Formula I described hereinabove in Example 1 was drawn on Form 2A Leneta cards to form a layer of about 10 mils in thickness. Gloss measurement was then taken over light and dark areas of the layer using a Micro-Gloss® glossmeter (from BYK-Gardner at Columbia, Md.) at a 60° angle. Specifically, two measurements were taken over the dark area and a third was taken over the light area. The three measurements were then averaged to provide a glass reading in terms of gloss units (i.e., gu). The higher the number of gloss units, the more glossy the layer.

The gloss measurement results so obtained are tabulated as follows:

| Measurement | Gloss Reading (gu) |
|---|---|
| 1 | 86.00 |
| 2 | 86.30 |
| 3 | 86.60 |
| Average | 86.3 |

EXAMPLE 3

Drop Point Measurement

The drop point of a lipstick formed according to Formula I described hereinabove in Example 1 was measured according to the following protocols:

Mettler-Toledo Drop Point Model FP90 Central Processor connected to FP83HT Dropping Point Cell (both manufactured by Mettler-Toledo AG at Greifensee, Switzerland) was used to determine the drop point of the lipstick formed from the composition specified as Formula I hereinabove. The lipstick was melted completely to a liquid state and poured into a measuring cup, held down undisturbed at 25° C. for 24 hours, and then placed into the above-mentioned Mettler-Toledo equipment, which was programmed to start heating at 40° C. with rate of 2° C./min up to 100° C. When the mass was re-liquefied in the furnace, it released the first drop at a specific temperature. This temperature was recorded as the Drop Point Temperature. For the lipstick formed from Formula I, the Drop Point was approximately 76° C.

EXAMPLE 4

Break Point Measurement

The break point of a lipstick formed according to Formula I described hereinabove in Example 1 was measured by using a Cavalla/Model #1009 (manufactured by Cavalla Inc. at Hackensack, N.J.). The lipstick, as freshly made, was incubated at 25° C. for 24 hours before testing. Lipstick's cap was removed, and the lipstick was swiveled all the way out and then placed in a holder together with the lipstick case. The gauge needles of the Cavalla were set on zero, and the motor of the Cavalla was turned on. After the lipstick broke transversally, the breakage point was read directly from the black needle points on Cavalla scale.

The amount of force required for breaking the lipstick (i.e., the breakage point) was approximately 13.3 pounds.

EXAMPLE 5

Crush Point Measurement

The crush point of a lipstick formed according to Formula I described hereinabove in Example 1 was measured by using a CHATILLON® LTCM-2 series force tester (from Ametek U.S. at Largo, Fla.). The lipstick, as freshly made, was incubated at 25° C. for 24 hours before testing and then placed inside a glassine envelope. The instrument speed was set at 5, and the gauge needle was placed on zero. The glassine envelope containing the lipstick was placed between the plates of the force tester. The motor of the tester was turned on and allowed to run until the gauge stops moving, which occurs approximately 30-60 seconds, and the crush point was read directly from the gauge of the force tester.

The amount of force required for crushing the lipstick (i.e., the crush point) was approximately 2.4 kilograms.

Although the invention has been variously disclosed herein with reference to illustrative embodiments and features, it will be appreciated that the embodiments and features described hereinabove are not intended to limit the scope of the invention, and that other variations, modifications and other embodiments will suggest themselves to those of ordinary skill in the art. The invention therefore is to be broadly construed, consistent with the claims hereafter set forth.

What is claimed is:

1. A cosmetic composition comprising:
   (a) a first oil component having a first viscosity in the range of from about 100 centipoises to about 300 centipoises at about 25° C., in an amount ranging from about 20 wt % to about 80 wt % by total weight of the composition;
   (b) a second oil component having a second viscosity that is lower than the first viscosity, the second viscosity being in the range of from about 10 centipoises to about 100 centipoises at about 25° C., in amount ranging from about 0.1 wt % to about 5 wt % by total weight of the composition;
   (c) a third oil component having a third viscosity that is lower than the second viscosity, the third viscosity being in the range of from about 0.1 centipoises to about 100 centipoises at about 25° C., in an amount ranging from about 0.1 wt % to about 5 wt % by total weight of the composition;
   (d) an oily gelling agent comprising a glycerol ester of behenic acid and eicosanoic diacid in an amount ranging from about 0.5 wt % to about 2 wt % by total weight of the composition,
   (e) organic and/or inorganic pigment in an amount ranging from about 10 wt % to about 20 wt %; and if present,
   (f) inorganic powder in an amount ranging from about 0.5 to about 5.0 wt %;
   wherein said cosmetic composition is characterized by a gloss of at least 85 gloss units (gu), said cosmetic composition containing less than 8 wt % of waxes by total weight of the composition and having sufficient shape retention properties for forming a stick-shaped cosmetic product.

2. The cosmetic composition of claim 1, wherein the first oil component comprises one or more oils selected from the group consisting of tridecyl trimellitate, diisostearyl malate, triisostearyl citrate, polyglyceryl-2-triisostearate, and combinations thereof.

3. The cosmetic composition of claim 1, wherein the second oil component comprises one or more oils selected from the group consisting of caprylic/capric triglyceride, pentaerythrityl tetraisostearate, octyldodecyl lactate, PPG-3 benzyl myristate ether, and combinations thereof.

4. The cosmetic composition of claim 1, wherein the third oil component comprises one or more oils selected from the group consisting of octyldodecyl neopentanoate, tridecyl octanoate, isopropyl isostearate, isodecyl isononanoate, and combinations thereof.

5. The cosmetic composition of claim 1, which is characterized by a drop point of not less than about 50° C.

6. The cosmetic composition of claim 1, further comprising one or more gels selected from the group consisting of bis-diglyceryl polyacyladipate-2, dipentaerythrityl tetrabehenate/polyhydroxystearate, dextrin palmitate, dibutyl lauroyl glutamide, ethyl cellulose, and combinations thereof.

7. The cosmetic composition of claim 6, wherein said one or more gels are present in said composition at a total amount ranging from about 2 wt % to about 40 wt % by total weight of the composition.

8. The cosmetic composition of claim 7, comprising bis-diglyceryl polyacyladipate-2 at an amount ranging from about 5 wt % to about 10 wt % by total weight of the composition and dipentaerythrityl tetrabehehate/polyhydroxystearate at an amount ranging from about 5 wt % to about 10 wt % by total weight of the composition.

9. The cosmetic composition of claim 1, further comprising a pasty component having a melting temperature or a drop point ranging from about 32° C. to about 42° C.

10. The cosmetic composition of claim 9, wherein said pasty component is selected from the group consisting of caprylic/capric/myristic/stearic triglyceride, cetyl lactate, lanolin, shea butter, and combinations thereof.

11. The cosmetic composition of claim 10, wherein said pasty component is present in said composition at an amount ranging from about 2 wt % to about 20 wt % by total weight of the composition.

12. The cosmetic composition of claim 11, comprising caprylic/capric/myristic/stearic triglyceride at an amount ranging from about 5 wt % to about 10 wt % by total weight of the composition.

13. The cosmetic composition of claim 1, further comprising a liquid film former and a solid film former.

14. The cosmetic composition of claim 13, wherein the liquid film former is selected from the group consisting of PVP/hexadecene copolymer, polyglyceryl-2 diisostearate/isophorone diisocyanate (IPDI) copolymer, liquid wax, methyl hydrogenated rosinate, and combinations thereof and is present in said composition at an amount ranging from about 0.01 wt % to about 2 wt % by total weight of the composition, and wherein the solid film former is selected from the group consisting of PVP/eicosene copolymer, tricontanyl PVP, $C_{20}$-$C_{40}$ alcohols, glyceryl rosinate, and combinations thereof and is present in said composition at an amount ranging from about 0.5 wt % to about 5 wt % by total weight of the composition.

15. The cosmetic composition of claim 14, comprising PVP/hexadecene copolymer at an amount ranging from about 0.1 wt % to about 0.5 wt % by total weight of the composition and PVP/eicosene copolymer at an amount ranging from about 1 wt % to about 2 wt % by total weight of the composition.

16. A stick-shaped cosmetic product formed by the cosmetic composition of claim 1, wherein said cosmetic stick is characterized by a drop point of at least 70° C.

17. A method of forming a stick-shaped cosmetic product, comprising the steps of:
  (a) providing a cosmetic composition according to claim 1;
  (b) pouring said cosmetic composition into a mold having one or more stick-shaped cavities; and
  (c) allowing the cosmetic composition to solidify in the mold, thereby forming one or more stick-shaped cosmetic products.

* * * * *